US006451747B1

(12) United States Patent
Decoster

(10) Patent No.: US 6,451,747 B1
(45) Date of Patent: *Sep. 17, 2002

(54) DETERGENT COSMETIC COMPOSITIONS FOR HAIR CARE AND UTILISATION THEREOF

(75) Inventor: Sandrine Decoster, Epinay sur Seine (FR)

(73) Assignee: L'Oreal S.A., Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,966

(22) PCT Filed: Jun. 6, 1997

(86) PCT No.: PCT/FR97/01007

§ 371 (c)(1),
(2), (4) Date: Jan. 12, 1999

(87) PCT Pub. No.: WO97/46210

PCT Pub. Date: Dec. 11, 1997

(30) Foreign Application Priority Data

Jun. 7, 1996 (FR) .............................. 96 07192

(51) Int. Cl.$^7$ .............................. A61K 7/075; A61K 7/50
(52) U.S. Cl. .................. 510/119; 510/121; 510/122; 510/123; 510/126; 510/129; 510/466; 510/475; 510/504; 424/401; 424/70.1; 424/70.12; 424/70.122; 424/70.13; 424/70.15; 424/70.16; 424/70.17; 424/70.19
(58) Field of Search ............................ 510/119, 121, 510/122, 123, 126, 129, 466, 475, 504; 424/401, 70.1, 70.12, 70.122, 70.13, 70.15, 70.16, 70.17, 70.19

(56) References Cited

U.S. PATENT DOCUMENTS

| | | | | |
|---|---|---|---|---|
| 2,261,002 A | 10/1941 | Ritter | ........................ | 260/570 |
| 2,271,378 A | 1/1942 | Searle | ........................ | 167/22 |
| 2,273,780 A | 2/1942 | Dittmar | ........................ | 260/28 |

(List continued on next page.)

FOREIGN PATENT DOCUMENTS

| | | |
|---|---|---|
| EP | 0 095 238 | 11/1983 |
| EP | 0 122 234 | 10/1984 |
| EP | 0 337 354 | 10/1989 |
| EP | 0 412 704 | 2/1991 |
| EP | 0 412 707 | 2/1991 |
| EP | 0 582 152 | 2/1994 |
| FR | 1 492 597 | 8/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 393 573 | 1/1979 |
| FR | 2 413 907 | 8/1979 |
| FR | 2 470 596 | 6/1981 |
| FR | 2 519 863 | 7/1983 |
| FR | 2 598 611 | 11/1987 |
| WO | WO 92/16179 | 10/1992 |
| WO | WO 93/23009 | * 11/1993 |
| WO | WO 93/23446 | 11/1993 |
| WO | WO 95/00478 | 1/1995 |
| WO | WO 95/00578 | 1/1995 |
| WO | WO 95/03776 | 2/1995 |
| WO | WO 95/05800 | * 3/1995 ............ A61K/7/48 |

OTHER PUBLICATIONS

M. R. Porter, "Handbook of Surfactants", published by Blackie & Son (Glasgow and London), 1991, pp. 116–178. No month given.
English language Derwent Abstract of FR 1 583 363, Oct. 24, 1969.
English language Derwent Abstract of FR 2 077 143, Oct. 15, 1971.
English language Derwent Abstract of FR 2 080 759, Nov. 19, 1971.
English language Derwent Abstract of FR 2 162 025, Jul. 13, 1973.
English language Derwent Abstract of FR 2 190 406, Feb. 1, 1974.
English language Derwent Abstract of FR 2 252 840, Jun. 27, 1975.
English language Derwent Abstract of FR 2 270 846, Dec. 12, 1975.
English language Derwent Abstract of FR 2 280 361, Feb. 27, 1976.
English language Derwent Abstract of FR 2 316 271, Jan. 28, 1977.

(List continued on next page.)

Primary Examiner—Yogendra N. Gupta
Assistant Examiner—Brian P. Mruk
(74) Attorney, Agent, or Firm—Finnegan, Henderson, Farabow, Garrett and Dunner, L.L.P.

(57) ABSTRACT

The invention discloses novel detergent and conditioning hair care compositions comprising, in a cosmetically acceptable medium, (A) a washing base and (B) a conditioning system comprising at least one cationic polymer and a mixture of at least one amine silicone and of at least one grafted silicone polymer comprising one polysiloxane portion and one portion constituted by one non-silicone-modified organic chain, one of the two portions constituting the primary polymer chain, the other being grafted on the primary chain. These compositions have improved hairstyling effect. The invention is useful for hair washing, care and styling.

77 Claims, No Drawings

U.S. PATENT DOCUMENTS

| | | | | |
|---|---|---|---|---|
| 2,375,853 | A | 5/1945 | Kirby et al. | 260/583 |
| 2,388,614 | A | 11/1945 | Kirby et al. | 167/22 |
| 2,454,547 | A | 11/1948 | Bock et al. | 260/567.6 |
| 2,961,347 | A | 11/1960 | Floyd | 117/141 |
| 3,206,462 | A | 9/1965 | McCarty | 260/256.4 |
| 3,227,615 | A | 1/1966 | Korden | 167/87.1 |
| 3,874,870 | A | 4/1975 | Green et al. | 71/67 |
| 3,929,990 | A | 12/1975 | Green et al. | 424/78 |
| 3,966,904 | A | 6/1976 | Green et al. | 424/78 |
| 4,001,432 | A | 1/1977 | Green et al. | 424/329 |
| 4,005,193 | A | 1/1977 | Green et al. | 424/168 |
| 4,025,617 | A | 5/1977 | Green et al. | 424/78 |
| 4,025,627 | A | 5/1977 | Green et al. | 424/248.4 |
| 4,025,653 | A | 5/1977 | Green et al. | 424/325 |
| 4,026,945 | A | 5/1977 | Green et al. | 260/567.6 P |
| 4,031,307 | A | 6/1977 | DeMartino et al. | 536/114 |
| 4,131,576 | A | 12/1978 | Iovine et al. | 260/17.466 |
| 4,185,087 | A | 1/1980 | Morlino | 424/70 |
| 4,693,935 | A | 9/1987 | Mazurek | 428/352 |
| 4,728,571 | A | 3/1988 | Clemens et al. | 428/352 |
| 4,972,037 | A | 11/1990 | Garbe et al. | 526/245 |
| 5,567,428 | A * | 10/1996 | Hughes | 424/401 |
| 5,976,517 | A * | 11/1999 | Dubief et al. | 424/70.1 |
| 6,022,836 | A * | 2/2000 | Dubief et al. | 510/122 |

OTHER PUBLICATIONS

English language Derwent Abstract of FR 2 320 330, Mar. 4, 1977.

English language Derwent Abstract of FR 2 336 434, Jul. 22, 1977.

English language Derwent Abstract of FR 2 368 508, May 19, 1978.

English language Derwent Abstract of FR 2 393 573, Jan. 5, 1979.

English language Derwent Abstract of FR 2 413 907, Aug. 3, 1979.

English language Derwent Abstract of FR 2 470 596, Jun. 12, 1981.

English language Derwent Abstract of FR 2 519 863, Jul. 22, 1983.

English language Derwent Abstract of FR 2 598 611, Nov. 20, 1987.

* cited by examiner

DETERGENT COSMETIC COMPOSITIONS FOR HAIR CARE AND UTILISATION THEREOF

The present invention relates to novel cosmetic compositions with improved properties, intended both for cleaning, conditioning and styling the hair, and comprising, in a cosmetically acceptable vehicle, a washing base consisting of surfactants with detergent power, in which cationic polymers in combination with specific silicones are also present as conditioners. The invention also relates to the use of the said compositions in the abovementioned cosmetic application.

It is common to use detergent hair compositions (or shampoos) based essentially on standard surfactants of anionic, nonionic and/or amphoteric type in particular, but more particularly of anionic type, to clean and/or wash the hair. These compositions are applied to wet hair and the lather generated by massaging or rubbing with the hands removes, after rinsing with water, the various types of soiling which are initially present on the hair.

Admittedly these base compositions are of good washing power, but the intrinsic cosmetic properties associated with them nevertheless remain fairly poor, owing in particular to the fact that the relatively aggressive nature of such a cleaning treatment can, in the long run, lead to more or less pronounced damage to the hair fibre, this damage being associated in particular with the gradual removal of the lipids or proteins contained in or on the surface of this fibre.

Thus, in order to improve the cosmetic properties of the above detergent compositions, and more particularly those which are intended to be applied to sensitized hair (i.e. hair which has been damaged or made brittle, in particular under the chemical action of atmospheric agents and/or hair treatments such as permanent-waving, dyeing or bleaching), it is now common to introduce additional cosmetic agents known as conditioners into these compositions, these conditioners being intended mainly to repair or limit the harmful or undesirable effects induced by the various treatments or aggressions to which the hair fibres are subjected more or less repeatedly. These conditioners may, of course, also improve the cosmetic behaviour of natural hair.

The conditioners most commonly used to date in shampoos are cationic polymers, which give washed, dry or wet hair an ease of disentangling, softness and smoothness which are markedly better than that which can be obtained with corresponding cleaning compositions from which they are absent.

Moreover, it has for some time been sought to obtain conditioning shampoos which are capable of giving washed hair not only the cosmetic properties mentioned above but also, to a greater or lesser extent, styling, volume, shaping and hold properties. These washing shampoos with improved general cosmetic properties are often referred to for simplicity as "styling shampoos", and this expression will be adopted in the description hereinbelow.

However, despite the progress made recently in the field of styling shampoos based on cationic polymers, these shampoos are not really completely satisfactory, and as such a strong need still exists currently as regards being able to provide novel products which give better performance with respect to one or more of the cosmetic properties mentioned above.

The present invention is directed towards satisfying such a need.

Thus, after considerable research conducted in this matter, the Applicant has now found, entirely surprisingly and unexpectedly, that by using (A) a washing base and (B) a conditioning system comprising at least one cationic polymer and at least one mixture of suitably selected specific silicones, as defined below, it is possible to obtain detergent compositions which give excellent cosmetic properties, in particular ease of styling, hold, liveliness and volume to the hair treated, while at the same time retaining their good intrinsic washing power.

All of these discoveries form the basis of the present invention.

Thus, according to the present invention, novel detergent and conditioning hair compositions are now proposed, comprising, in a cosmetically acceptable medium, (A) a washing base and (B) a conditioning system comprising at least one cationic polymer and a mixture of at least one grafted silicone polymer comprising a polysiloxane portion and a portion consisting of a non-silicone organic chain, one of the two portions constituting the main chain of the polymer, the other being grafted onto the said main chain, and at least one aminosilicone.

A subject of the invention is also the cosmetic use of the above compositions for cleaning, conditioning and/or styling the hair.

However, other characteristics, aspects and advantages of the invention will emerge even more clearly on reading the description which follows, as well as the concrete, but in no way limiting, examples intended to illustrate it.

As indicated above, the essential constituents forming part of the composition of the hair products of the invention are (A) a washing base, (B) a conditioning system comprising (i) the cationic polymer(s), and (ii) a mixture of at least one grafted silicone polymer and at least one aminosilicone.

A—WASHING BASE

The compositions in accordance with the invention necessarily comprise a washing base, which is generally aqueous.

The surfactant(s) forming the washing base can be chosen, indifferently, alone or as mixtures, from anionic, amphoteric, nonionic, zwitterionic and cationic surfactants.

The minimum amount of washing base is that which is just sufficient to give the final composition a satisfactory foaming and/or detergent power, and excessive amounts of washing base will not really give any additional advantages.

Thus, according to the invention, the washing base can represent from 4% to 50% by weight, preferably from 10% to 35% by weight and even more preferably from 12% to 25% by weight, of the total weight of the final composition.

The surfactants which are suitable for carrying out the present invention are in particular the following:

(i) Anionic Surfactant(s):

In the context of the present invention, their nature is not a truly critical feature.

Thus, as examples of anionic surfactants which can be used, alone or as mixtures, in the context of the present invention, mention may be made in particular (non-limiting list) of salts (in particular alkaline salts, especially sodium salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates, the alkyl or acyl radical of all of these various compounds preferably containing from 12 to 20 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Use may also be made of weakly anionic surfactants, such as alkyl-D-galactosiduronic acids and their salts, as well as polyoxyalkylenated carboxylic ether acids and their salts, in particular those containing from 2 to 50 ethylene oxide groups, and mixtures thereof. Anionic surfactants of the polyoxyalkylenated carboxylic ether acid or salt type are, in particular, those which correspond to formula (1) below:

$$R_1-(OC_2H_4)_n-OCH_2COOA \qquad (1)$$

in which:

$R_1$ denotes an alkyl or alkaryl group, and n is an integer or decimal (average value) which can range from 2 to 24 and preferably from 3 to 10, the alkyl radical having between 6 and 20 carbon atoms approximately, and aryl preferably denoting phenyl.

A denotes H, ammonium, Na, K, Li, Mg or a monoethanolamine or triethanolamine residue. Mixtures of compounds of formula (1) can also be used, in particular mixtures in which the groups $R_1$ are different.

Among the anionic surfactants, it is preferred to use alkyl sulphate salts and alkyl ether sulphate salts.

(ii) Nonionic Surfactant(s):

Nonionic surfactants are likewise compounds that are well known per se (see in particular in this respect "Handbook of Surfactants" by M. R. Porter, published by Blackie & Son (Glasgow and London), 1991, pp. 116–178) and, in the context of the present invention, their nature is not a critical feature. Thus, they can be chosen in-particular from (non-limiting list) polyethoxylated, polypropoxylated or polyglycerolated fatty acids, alkylphenols, α-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable in the context of the present invention.

(iii) Amphoteric or Zwitterionic Surfactant(s):

The amphoteric or zwitterionic surfactants, whose nature is not a critical feature in the context of the present invention, can be, in particular (non-limiting list), aliphatic secondary or tertiary amine derivatives in which the aliphatic radical is a linear or branched chain containing 8 to 18 carbon atoms and containing at least one water-soluble anionic group (for example carboxylate, sulphonate, sulphate, phosphate or phosphonate); mention may also be made of ($C_8$–$C_{20}$)alkylbetaines, sulphobetaines, ($C_8$–$C_{20}$) alkylamido($C_1$–$C_6$)alkylbetaines or ($C_{8-20}$) alkylamido ($C_1$–$C_6$) alkylsulphobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

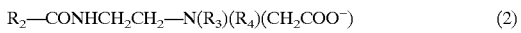

$$R_2-CONHCH_2CH_2-N(R_3)(R_4)(CH_2COO^-) \qquad (2)$$

in which: $R_2$ denotes an alkyl radical of an acid $R_2$—COOH present in hydrolysed coconut oil, a heptyl, nonyl or undecyl radical, $R_3$ denotes a β-hydroxyethyl group and $R_4$ a carboxymethyl group;

and

$$R_2'-CONHCH_2CH_2-N(B)(C) \qquad (3)$$

in which:

B represents —$CH_2CH_2OX'$, C represents —$(CH_2)_z$—Y', with z=1 or 2,

X' denotes the —$CH_2CH_2$—COOH group or a hydrogen atom,

Y' denotes —COOH or the —$CH_2$—CHOH—$SO_3$H radical, $R_2'$ denotes an alkyl radical of an acid $R_9$ —COOH present in coconut oil or in hydrolysed linseed oil, an alkyl radical, in particular a $C_7$, $C_9$, $C_{11}$ or $C_{13}$ alkyl radical, a $C_{17}$ alkyl radical and its iso form, or an unsaturated $C_{17}$ radical.

For example, mention may be made of cocoamphocarboxyglycinate sold under the trade name Miranol C2M concentrate by the company Miranol.

(iv) Cationic Surfactants:

Among the cationic surfactants, mention may be made in particular of (non-limiting list): optionally polyoxyalkylenated primary, secondary or tertiary fatty amine salts; quaternary ammonium salts such as tetraalkylammonium, alkylamidoalkyltrialkyl-ammonium, trialkylbenzylammonium, trialkylhydroxyalkyl-ammonium or alkylpyridinium chlorides or bromides; imidazoline derivatives; or amine oxides of cationic nature.

It will be noted that the cationic surfactants, the use of which is not excluded, do not constitute preferred surfactants for carrying out the present invention.

B—CONDITIONING SYSTEM (i) Cationic Polymer(s):

The compositions in accordance with the invention also necessarily comprise a cationic polymer.

The conditioners of cationic polymer type which can be used in accordance with the present invention can be chosen from any of those already known per se as improving the cosmetic properties of hair treated with detergent compositions, namely, in particular, those described in patent application EP-A-0,337,354 and in French patent applications FR-A-2,270,846, 2,383,660, 2,598,611, 2,470, 596 and 2,519,863.

Even more generally, for the purposes of the present invention, the expression "cationic polymer" denotes any polymer containing cationic groups and/or groups which can be ionized into cationic groups.

The preferred cationic polymers are chosen from those which contain units containing primary, secondary, tertiary and/or quaternary amine groups which can either form part of the main polymer chain or be borne by a side substituent that is directly attached to the latter.

The cationic polymers used generally have a number-average molecular mass of between 500 and $5 \times 10^6$ approximately and preferably between $10^3$ and $3 \times 10^6$ approximately.

Among the cationic polymers, mention may be made more particularly of quaternized proteins (or protein hydrolysates) and polymers of the polyamine, polyaminoamide and polyquaternary ammonium type. These are known products.

The quaternized proteins or protein hydrolysates are, in particular, chemically modified polypeptides bearing quaternary ammonium groups at the end of the chain or grafted thereto. Their molecular mass can range, for example, from 1500 to 10,000 and in particular from 2000 to 5000 approximately. Among these compounds, mention may be made in particular of:

collagen hydrolysates bearing triethylammonium groups, such as the products sold under the name "Quat-Pro E" by the company Maybrook and referred to in the CTFA dictionary as "Triethonium Hydrolyzed Collagen Ethosulfate";

collagen hydrolysates bearing trimethylammonium and trimethylstearylammonium chloride groups, sold under the name "Quat-Pro S" by the company Maybrook and referred to in the CTFA dictionary as "Steartrimonium Hydrolyzed Collagen";

animal protein hydrolysates bearing trimethylbenzylammonium groups such as the products sold under the name "Crotein BTA" by the company Croda and referred to in the CTFA dictionary as "Benzyltrimonium hydrolyzed animal protein";

protein hydrolysates bearing, on the polypeptide chain, quaternary ammonium groups containing at least one alkyl radical having from 1 to 18 carbon atoms.

Among these protein hydrolysates, mention may be made of, inter alia:

"Croquat L" in which the quaternary ammonium groups contain a $C_{12}$ alkyl group;

"Croquat M" in which the quaternary ammonium groups contain $C_{10}$–$C_{18}$ alkyl groups;

"Croquat S" in which the quaternary ammonium groups contain a $C_{18}$ alkyl group;

"Crotein Q" in which the quaternary ammonium groups contain at least one alkyl group having from 1 to 18 carbon atoms.

These various products are sold by the company Croda.

Other quaternized proteins or hydrolysates are, for example, those corresponding to the formula:

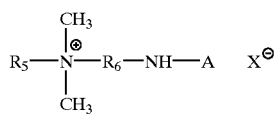

(I)

in which x⁻ is an anion of an organic or inorganic acid, A denotes a protein residue derived from collagen protein hydrolysates, $R_5$ denotes a lipophilic group containing up to 30 carbon atoms and $R_6$ represents an alkylene group having 1 to 6 carbon atoms. Mention may be made, for example, of the products sold by the company Inolex under the name "Lexein QX 3000", referred to in the CTFA dictionary as "Cocotrimonium Collagen Hydrolysate".

Mention may also be made of quaternized plant proteins such as wheat, corn or soybean proteins: as quaternized wheat proteins, mention may be made of those sold by the company Croda under the names "Hydrotriticum WQ or QM", referred to in the CTFA dictionary as "Cocodimonium Hydrolysed Wheat Protein", "Hydrotriticum QL", referred to in the CTFA dictionary as "Lauridimonium Hydrolysed Wheat Protein" or "Hydrotriticum QS", referred to in the CTFA dictionary as "Steardimonium Hydrolysed Wheat Protein".

The polymers of the polyquaternary ammonium, polyamidoamide and polyamine type which can be used in accordance with the present invention and which may be mentioned in particular are those described in French patents Nos. 2,505,348 and 2,542,997. Of these polymers, the following may be mentioned:

(1) Quaternized or non-quaternized vinylpyrrolidone/ dialkylaminoalkyl acrylate or methacrylate copolymers, such as the products sold under the name "Gafquat" by the-company ISP such as, for example, Gafquat 734, 755 or HS100 or alternatively the product known as "Copolymére 937". These polymers are described in detail in French patents 2,077,143 and 2,393,573.

(2) The cellulose ether derivatives containing quaternary ammonium groups, described in French patent 1,492,597, and in particular the polymers sold under the names "JR" (JR 400, JR 125 and JR 30M) or "LR" (LR 400, and LR 30M) by the company Union Carbide Corporation. These polymers are also defined in the CTFA dictionary as quaternary ammoniums of hydroxyethylcellulose which has reacted with an epoxide substituted with a trimethylammonium group.

(3) Cationic cellulose derivatives such as cellulose copolymers or cellulose derivatives grafted with a water-soluble monomer of quaternary ammonium, and described in particular in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

The commercial products corresponding to this definition are more particularly the products sold under the name "Celquat L 200" and "Celquat H 100" by the company National Starch.

(4) The cationic polysaccharides described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example.

Such products are sold in particular under the trade names Jaguar C13 S, Jaguar C 15, Jaguar C 17 or Jaguar C162 by the company Meyhall.

(5) Polymers consisting of piperazinyl units and of divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, in particular, in French patents 2,162,025 and 2,280,361;

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent is used in proportions ranging from 0.025 to 0.35 mol per amine group of the polymaoamide; these polyamino amides can be alkylated or, if they contain one or more tertiary amine functions, they can be quaternized. Such polymers are described, in particular, in French patents 2,252,840 and 2,368,508;

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialylenetriamine polymers in which the alkyl radical contains from 1 to 4 carbon atoms and preferably denotes methyl, ethyl or propyl. Such polymers are described in particular in French patent 1,583,363.

Among these derivatives, mention may be made more particularly of the adipic acid/dimethylaminohydroxypropyl/diethylenetriamine polymers sold under the name " Cartaretine F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett 57" by the company Hercules Inc. or alternatively under the name "PD 170" or "Delsette 101" by the company Hercules in the case of the adipic acid/epoxypropyl/diethylenetriamine copolymer.

(9) Cyclohomopolymers of methyldiallylamine or of dimethyldiallylammonium, such as the homopolymers containing, as main constituent of the chain, units corresponding to formula (VI) or (VI'):

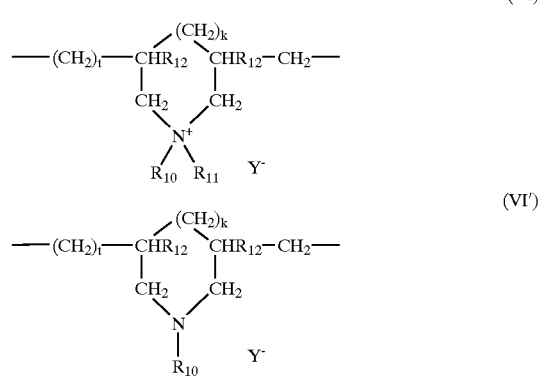

in which formulae k and t are equal to 0 or 1, the sum k+t being equal to 1; $R_{12}$ denotes a hydrogen atom or a methyl radical; $R_{10}$ and $R_{11}$, independently of each other, denote an alkyl group having from 1 to 22 carbon atoms, a hydroxyalkyl group in which the alkyl group preferably has 1 to 5 carbon atoms, or a lower amidoalkyl group, or $R_{10}$ and $R_{11}$ can denote, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate or phosphate. These polymers are described in particular in French patent 2,080,759 and in its Certificate of Addition 2,190,406.

Among the polymers defined above, mention may be made more particularly of the dimethyldiallylammonium chloride homopolymer sold under the name "Merquat 100" by the company Merck.

(10) The quaternary diammonium polymer containing repeating units corresponding to the formula:

in which formula (VII):

$R_{13}$, $R_{14}$, $R_{15}$ and $R_{16}$, which may be identical or different, represent aliphatic, alicyclic or arylaliphatic radicals containing from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ represent a linear or branched $C_{1-6}$ alkyl radical substituted with a nitrile, ester, acyl or amide group or a group —CO—O—$R_{17}$—D or —CO—NH—$R_{17}$—D where $R_{17}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and $X^-$ denotes an anion derived from an inorganic or organic acid;

$A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group $(CH_2)_n$—CO—D—OC—$(CH_2)_n$— in which D denotes:

a) a glycol residue of formula: —O—Z—O—, where Z denotes a linear or branched hydrocarbon-based radical or a group corresponding to one of the following formulae:

—(CH$_2$—CH$_2$—O)$_x$—CH$_2$—CH$_2$—

—[CH$_2$—CH(CH$_3$)—O]$_y$—CH$_2$—CH(CH$_3$)— where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or alternatively the divalent radical

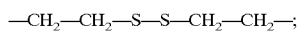
—CH$_2$—CH$_2$—S—S—CH$_2$—CH$_2$—;

d) a ureylene group of formula: —NH—CO—NH—.

Preferably, X$^-$ is an anion such as chloride or bromide.

These polymers generally have a number molecular mass of between 1000 and 100,000.

Polymers of this type are described in particular in French patents 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) Polyquaternary ammonium polymers consisting of units of formula (VIII):

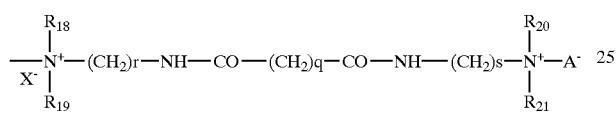

(VIII)

in which formula:

R$_{18}$, R$_{19}$, R$_{20}$ and R$_{21}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$OH radical, where p is equal to 0 or to an integer between 1 and 6, with the proviso that R$_{18}$, R$_{19}$, R$_{20}$ and R$_{21}$, do not simultaneously represent a hydrogen atom, r and s, which may be identical or different, are integers between 1 and 6, q is equal to 0 or to an integer between 1 and 34, X denotes a halogen atom, A denotes a dihalide radical or preferably represents —CH$_2$—CH$_2$—O—CH$_2$—CH$_2$—.

Such compounds are described in particular in patent application EP-A-122,324.

Among these products, mention may be made, for example, of "Mirapol A 15", "Mirapol AD1", "Mirapol AZ1" and "Mirapol 175" sold by the company Miranol.

(12) Homopolymers or copolymers derived from acrylic or methacrylic acids and containing units:

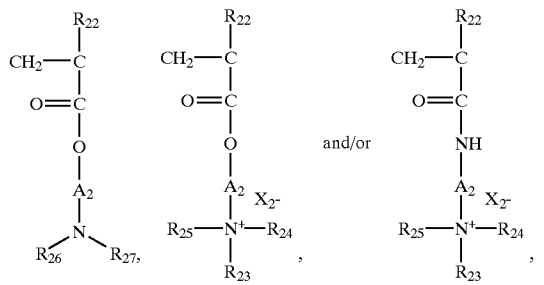

in which the groups R$_{22}$ independently denote H or CH$_3$, the groups A$_1$ independently denote a linear or branched alkyl group of 1 to 6 carbon atoms or a hydroxyalkyl group of 1 to 4 carbon atoms, the groups R$_{23}$, R$_{24}$, and R$_{25}$, which may be identical or different, independently denote an alkyl group of 1 to 18 carbon atoms or a benzyl radical, the groups R$_{26}$ and R$_{27}$, represent a hydrogen atom or an alkyl group of 1 to 6 carbon atoms, X$_2^-$ denotes an anion, for example methosulphate or halide, such as chloride or bromide.

The comonomer(s) which can be used in the preparation of the corresponding copolymers belong to the family of acrylamides, methacrylamides, diacetone acrylamides, acrylamides and methacrylamides substituted on the nitrogen with lower alkyls, alkyl esters, acrylic or methacrylic acids, vinylpyrrolidone or vinyl esters.

(13) Quaternary polymers of vinylpyrrolidone and of vinylimidazole, such as, for example, the products sold under the names Luviquat FC 905, FC 550 and FC 370 by the company BASF.

(14) Polyamines such as Polyquart H sold by Henkel, listed under the name "Polyethylene glycol (15) tallow polyamine" in the CTFA dictionary.

(15) Crosslinked methacryloyloxyethyltrimethylammonium chloride polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethyl ammonium chloride copolymer (20/80 by weight) in the form of a dispersion containing 50% by weight of the said copolymer in mineral oil can be used more particularly. This dispersion is sold under the name "Salcare SC 92" by the company Allied Colloids. A crosslinked methacryloyloxyethyltrimethylammonium chloride homopolymer containing about 50% by weight of the homopolymer in mineral oil can also be used. This dispersion is sold under the name "Salcare SC 95" by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

According to the invention, polymers chosen from Mirapol, the compound of formula (VII) in which R$_{13}$, R$_{14}$, R$_{15}$ and R$_{16}$ represent a methyl radical, A$_1$ represents a radical of formula —(CH$_2$)$_3$— and B$_1$ represents a radical of formula —(CH$_2$)$_6$— and X$^-$ represents a chloride anion (referred to hereinbelow as Mexomer PO) and the compound of formula (VII) in which R$_{13}$ and R$_{14}$, represent an ethyl radical, R$_{15}$, and R$_{16}$ represent a methyl radical, A$_1$ and B$_1$ represent a radical of formula —(CH$_2$)$_3$—and X$^-$ represents a bromide anion (referred to hereinbelow as Mexomer PAK) can be used more particularly.

Among all the cationic polymers which can be used in the context of the present invention, it is preferred to use quaternary cellulose ether derivatives such as the products sold under the name "JR 400" by the company Union Carbide Corporation, cyclopolymers, in particular the copolymers of dimethyldiallylammonium chloride and of acrylamide, sold under the names "Merquat 550" and "Merquat S" by the company Merck, cationic polysaccharides and more particularly guar gum modified with 2,3-epoxypropyltrimethylammonium chloride sold under the name "Jaguar C13S" by the company Meyhall.

According to the invention, the cationic polymer(s) can represent from 0.001% to 10% by weight, preferably from 0.005% to 5% by weight and even more preferably from 0.01% to 3% by weight, relative to the total weight of the final composition.

(ii)—Mixture of Silicones

According to an essential characteristic of the detergent hair compositions in accordance with the invention, these compositions also contain a mixture of at least one specific silicone of grafted silicone polymer type and at least one aminosilicone (different from the previous one).

(1) Grafted Silicone Polymers

According to an essential characteristic of the detergent hair compositions in accordance with the invention, these compositions also contain at least one grafted silicone polymer.

The grafted silicone polymers according to the invention are preferably chosen from polymers having a non-silicone organic skeleton grafted with monomers containing a polysiloxane, polymers having a polysiloxane skeleton grafted with non-silicone organic monomers and mixtures thereof.

In the following or preceding text, in accordance with what is generally accepted, the term silicone or polysiloxane is understood to denote any organosilicon polymer or oligomer having a linear or cyclic, branched or crosslinked structure of variable molecular weight, obtained by polymerization and/or polycondensation of suitably functionalized silanes, and consisting essentially of a repetition of main units in which the silicon atoms are linked together by oxygen atoms (siloxane bonding ≡Si—O—Si≡), optionally substituted hydrocarbon radicals being linked directly via a carbon atom to the said silicon atoms. The most common hydrocarbon radicals are alkyl radicals, especially $C_1$–$C_{10}$ alkyl radicals, and in particular methyl, fluoroalkyl radicals, aryl radicals and in particular phenyl, and alkenyl radicals and in particular vinyl; other types of radicals which can be linked, either directly or via a hydrocarbon radical, to the siloxane chain are, especially, hydrogen, halogens and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, substituted or unsubstituted amine groups, amide groups, acyloxy or acyloxyalkyl radicals, hydroxyalkylamino or aminoalkyl radicals, quaternary ammonium groups, amphoteric or betaine groups, anionic groups such as carboxylates, thioglycolates, sulphosuccinates, thiosulphates, phosphates and sulphates, needless to say this list not being limiting in any way (so-called "organomodified" silicones).

In the following text, in accordance with what is generally accepted, the expression "polysiloxane macromer" is understood to refer to any monomer containing a polysiloxane-type polymer chain in its structure.

The polymers containing a non-silicone organic skeleton grafted with monomers containing a polysiloxane, in accordance with the present invention, consist of an organic main chain formed from organic monomers containing no silicone, on which is grafted, inside the said chain and optionally on at least one of its ends, at least one polysiloxane macromer.

The non-silicone organic monomers constituting the main chain of the grafted silicone polymer can be chosen from monomers containing ethylenic unsaturation which are polymerizable via a radical route, monomers which are polymerizable by polycondensation, such as those forming polyamides, polyesters or polyurethanes, and monomers which involve ring opening, such as those of the oxazoline or caprolactone type.

The polymers containing a non-silicone organic skeleton grafted with monomers containing a polysiloxane, in accordance with the present invention, can be obtained according to any means known to those skilled in the art, in particular by reaction between (i) a starting polysiloxane macromer which is correctly functionalized on the polysiloxane chain and (ii) one or more non-silicone organic compounds, themselves correctly functionalized with a function which is capable of reacting with the functional group(s) borne by the said silicone, forming a covalent bond; a classic example of such a reaction is the radical reaction between a vinyl group borne on one of the ends of the silicone with a double bond of a monomer containing ethylenic unsaturation in the main chain.

The polymers containing a non-silicone organic skeleton grafted with monomers containing a polysiloxane, in accordance with the invention, are more preferably chosen from those described in U.S. Pat. Nos. 4,693,935, 4,728,571 and 4,972,037 and patent applications EP-A-0,412,704, EP-A-0,412,707, EP-A-0,640,105 and WO 95/00578. These are copolymers obtained by radical polymerization starting with monomers containing ethylenic unsaturation and silicone macromers having a terminal vinyl group, or alternatively copolymers obtained by reaction of a polyolefin comprising functionalized groups and a polysiloxane macromer having a terminal function which is reactive with the said functionalized groups.

One particular family of silicone grafted polymers which is suitable for carrying out the present invention consists of silicone grafted copolymers comprising:

a) from 0 to 98% by weight of at least one lipophilic monomer (A) of low lipophilic polarity containing ethylenic unsaturation, which is polymerizable via a radical route;

b) from 0 to 98% by weight of at least one polar hydrophilic monomer (B) containing ethylenic unsaturation, which is copolymerizable with the (A)-type monomer(s);

c) from 0.01 to 50% by weight of at least one polysiloxane macromer (C) of general formula:

$$X(Y)_n Si(R)_{3-m} Z_m \qquad (I)$$

where:

X denotes a vinyl group which is copolymerizable with the monomers (A) and (B);

Y denotes a divalent bonding group;

R denotes a hydrogen, a $C_1$–$C_6$ alkyl or alkoxy or a $C_6$–$C_{12}$ aryl;

Z denotes a monovalent polysiloxane unit having a number-average molecular weight of at least 500;

n is 0 or 1 and m is an integer ranging from 1 to 3; the percentages being calculated relative to the total weight of the monomers (A), (B) and (C).

These polymers are described, along with processes for their preparation, in U.S. Pat. Nos. 4,693,935, 4,728,571 and 4,972,037 and in patent applications EP-A-0,412,704, EP-A-0,412,707 and EP-A-0,640,105. They have a number-average molecular weight preferably ranging from 10,000 to 2,000,000 and preferably a glass transition temperature Tg or a crystalline melting point Tm of at least −20° C.

As examples of lipophilic monomers (A), mention may be made of acrylic or methacrylic acid esters of $C_1$–$C_{18}$ alcohols; styrene; polystyrene macromers; vinyl acetate; vinyl propionate;

α-methylstyrene; tert-butylstyrene; butadiene; cyclohexadiene; ethylene; propylene; vinyltoluene; acrylic or methacrylic acid esters of 1,1-dihydroperfluoroalkanol or of homologues thereof; acrylic or methacrylic acid esters of ω-hydridofluoroalkanol; acrylic or methacrylic acid esters of fluoroalkylsulphoamido alcohol; acrylic or methacrylic acid esters of fluoroalkyl alcohol; acrylic or methacrylic acid esters of fluoroether alcohol; or mixtures thereof.

The preferred monomers (A) are chosen from the group consisting of n-butyl methacrylate, isobutyl methacrylate, tert-butyl acrylate, tert-butyl methacrylate, 2-ethylhexyl methacrylate, methyl methacrylate, 2-(N-methylperfluorooctanesulphonamido)-ethyl acrylate and 2-(N-butylperfluorooctanesulphonamido)ethyl acrylate, and mixtures thereof.

As examples of polar monomers (B), mention may be made of acrylic acid, methacrylic acid, N,N-dimethylacrylamide, dimethylaminoethyl methacrylate, quaternized dimethylaminoethyl methacrylate, (meth)acrylamide, N-t-butylacrylamide, maleic acid, maleic anhydride and semiesters thereof, hydroxyalkyl (meth)acrylates, diallyldimethylammonium chloride, vinylpyrrolidone, vinyl ethers, maleimides, vinylpyridine, vinylimidazole, heterocyclic vinyl polar compounds, styrene sulphonate, allyl alcohol, vinyl alcohol and vinyl caprolactam, or mixtures thereof. The preferred monomers (B) are chosen from the group consisting of acrylic acid, N,N-dimethylacrylamide, dimethylaminoethyl methacrylate, quaternized dimethylaminoethyl methacrylate and vinylpyrrolidone, and mixtures thereof.

The preferred polysiloxane macromers (C) of formula (I) are chosen from those corresponding to the general formula (II) below:

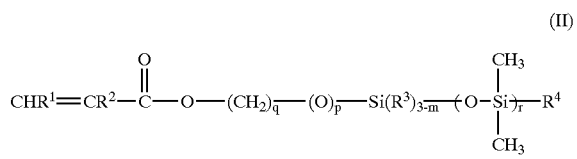

(II)

in which:

$R^1$ is hydrogen or —COOH (preferably hydrogen);

$R^2$ is hydrogen, methyl or —CH$_2$COOH (preferably methyl);

$R^3$ is $C_1$–$C_6$ alkyl, alkoxy, or alkylamino, $C_6$–$C_{12}$ aryl or hydroxyl (preferably methyl);

$R^4$ is $C_{1-6}$ alkyl, alkoxy or alkylamino, $C_6$–$C_{12}$ aryl or hydroxyl (preferably methyl);

q is an integer from 2 to 6 (preferably 3);

p is 0 or 1;

r is an integer from 5 to 700;

m is an integer ranging from 1 to 3 (preferably 1).

The polysiloxane macromers of formula:

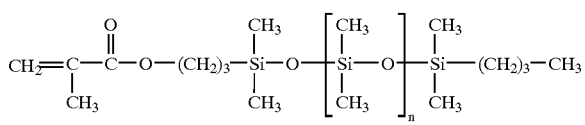

with n being a number ranging from 5 to 700, are more particularly used.

One particular embodiment of the invention consists in using a copolymer which can be obtained by radical polymerization starting with the monomer mixture consisting of:
a) 60% by weight of tert-butyl acrylate;
b) 20% by weight of acrylic acid;
c) 20% by weight of silicone macromer of formula:

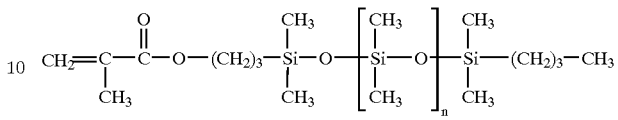

with n being a number ranging from 5 to 700; the weight percentages being calculated relative to the total weight of the monomers.

Another particular embodiment of the invention consists in using a copolymer which can be obtained by radical polymerization starting with the monomer mixture consisting of:
a) 80% by weight of tert-butyl acrylate;
b) 20% by weight of silicone macromer of formula:

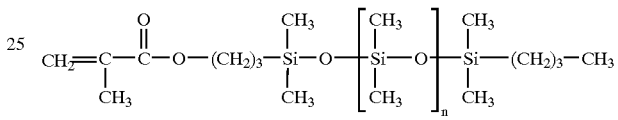

with n being a number ranging from 5 to 700; the weight percentages being calculated relative to the total weight of the monomers.

Another particular family of silicone polymers which is suitable for carrying out the present invention, consists of silicone grafted copolymers which can be obtained by reactive extrusion of a polysiloxane macromer having a terminal reactive function, on a polyolefin-type polymer containing reactive groups which can react with the terminal function of the polysiloxane macromer in order to form a covalent bond allowing grafting of the silicone to the main chain of the polyolefin.

These polymers are described, along with a process for their preparation, in patent application WO 95/00578.

The reactive polyolefins are preferably chosen from polyethylenes or polymers of ethylene-derived monomers such as propylene, styrene, alkylstyrene, butylene, butadiene, (meth)acrylates, vinyl esters or equivalents, containing reactive functions which can react with the terminal function of the polysiloxane macromer. They are chosen more particularly from copolymers of ethylene or of ethylene derivatives and of monomers chosen from those containing a carboxylic function, such as (meth)acrylic acid; those containing an acid anhydride function such as maleic anhydride; those containing an acid chloride function such as (meth)acryloyl chloride; those containing an ester function such as (meth)acrylic acid esters; those containing an isocyanate function.

The silicone macromers are preferably chosen from polysiloxanes containing a functionalized group, at the end of the polysiloxane chain or close to the end of the said chain, chosen from the group consisting of alcohols, thiols, epoxy groups and primary and secondary amines, and more particularly from those corresponding to the general formula:

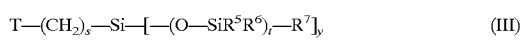

(III)

in which T is chosen from the group consisting of $NH_2$, NHR', an epoxy, OH, or SH function; $R^5$, $R^6$, $R^7$ and R', independently denote a $C_1$–$C_6$ alkyl, phenyl, benzyl, or $C_6$–$C_{12}$ alkylphenyl or hydrogen; s is a number from 2 to 100; t is a number from 0 to 1000 and y is a number from 1 to 3. They have a number-average molecular weight preferably ranging from 5000 to 300,000, more preferably from 8000 to 200,000 and more particularly from 9000 to 40,000.

According to the present invention, the grafted silicone polymer(s) containing a polysiloxane skeleton grafted with non-silicone organic monomers comprise a silicone (or polysiloxane ($\equiv$Si—O—)$_n$) main chain on which is grafted, inside the said chain and optionally on at least one of its ends, at least one organic group containing no silicone.

The polymers containing a polysiloxane skeleton grafted with non-silicone organic monomers, according to the invention, can be existing commercial products or alternatively can be obtained according to any means known to those skilled in the art, in particular by reaction between (i) a starting silicone which is correctly functionalized on one or more of these silicon atoms, and (ii) a non-silicone organic compound which is itself correctly functionalized with a function which is capable of reacting with the functional group(s) borne by the said silicone, forming a covalent bond; a classic example of such a reaction is the hydrosilylation reaction between $\equiv$Si—H groups and vinyl groups $CH_2$=CH—, or alternatively the reaction between thio functional groups —SH with these same vinyl groups.

Examples of polymers with a polysiloxane skeleton grafted with non-silicone organic monomers which are suitable for carrying out the present invention, as well as their specific mode of preparation, are described in particular in patent applications EP-A-0,582,152, WO 93/23009 and WO 95/03776, the teachings of which are included in their entirety in the present description by way of non-limiting references.

According to a particularly preferred embodiment of the present invention, the silicone polymer containing a polysiloxane skeleton grafted with non-silicone organic monomers, which is used comprises the result of the radical copolymerization between, on the one hand, at least one non-silicone anionic organic monomer having ethylenic unsaturation and/or a non-silicone hydrophobic organic monomer having ethylenic unsaturation, and, on the other hand, a silicone having in its chain at least one functional group capable of reacting with the said ethylenic unsaturations of the said non-silicone monomers, forming a covalent bond, in particular thio functional groups.

According to the present invention, the said anionic monomers containing ethylenic unsaturation are preferably chosen, alone or as mixtures, from linear or branched, unsaturated carboxylic acids, optionally partially or totally neutralized in the form of a salt, it being possible for this (these) unsaturated carboxylic acid(s) to be, more particularly, acrylic acid, methacrylic acid, maleic acid, maleic anhydride, itaconic acid, fumaric acid and crotonic acid. The suitable salts are, in particular, alkali metal salts, alkaline-earth metal salts and ammonium salts. It will likewise be noted that, in the final grafted silicone polymer, the organic group of anionic nature which comprises the result of the radical (homo)polymerization of at least one anionic monomer of unsaturated carboxylic acid type can, after reaction, be post-neutralized with a base (sodium hydroxide, aqueous ammonia, etc.) in order to bring it into the form of a salt.

According to the present invention, the hydrophobic monomers containing ethylenic unsaturation are preferably chosen, alone or as mixtures, from acrylic acid esters of alkanols and/or methacrylic acid esters of alkanols. The alkanols are preferably $C_1$–$C_{18}$ and more particularly $C_1$–$C_{12}$. The preferred monomers are chosen from the group consisting of isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate and stearyl (meth)acrylate, or mixtures thereof.

One family of silicone polymers containing a polysiloxane skeleton grafted with non-silicone organic monomers which is particularly suitable for carrying out the present invention consists of silicone polymers containing in their structure the unit of formula (I) below:

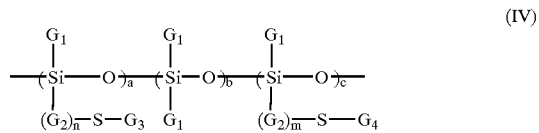

(IV)

in which the radicals $G_1$, which may be identical or different, represent hydrogen or a $C_1$–$C_{10}$ alkyl radical or alternatively a phenyl radical; the radicals $G_2$, which may be identical or different, represent a $C_1$–$C_{10}$ alkylene group; $G_3$ represents a polymer residue resulting from the (homo)polymerization of at least one anionic monomer containing ethylenic unsaturation; $G_4$ represents a polymer residue resulting from the (homo)polymerization of at least one hydrophobic monomer containing ethylenic unsaturation; m and n are equal to 0 or 1; a is an integer ranging from 0 to 50; b is an integer which may be between 10 and 350, c is an integer ranging from 0 to 50; with the proviso that one of the parameters a and c is other than 0.

Preferably, the unit of formula (IV) above has at least one, and even more preferably all, of the following characteristics:

the radicals $G_1$ denote an alkyl radical, preferably the methyl radical;

n is non-zero, and the radicals $G_2$ represent a divalent $C_1$–$C_3$ radical, preferably a propylene radical;

$G_3$ represents a polymer radical resulting from the (homo)polymerization of at least one monomer of the carboxylic acid type containing ethylenic unsaturation, preferably acrylic acid and/or methacrylic acid;

$G_4$ represents a polymer radical resulting from the (homo)polymerization of at least one monomer of the $C_1$–$_{10}$ alkyl (meth)acrylate type, preferably of the isobutyl or methyl (meth)acrylate type.

Examples of grafted silicone polymers corresponding to formula (IV) are, in particular, polydimethylsiloxanes (PDMS) on which are grafted, via a thiopropylene-type connecting chain, mixed polymer units of the poly(meth) acrylic acid type and of the polymethyl (meth)acrylate type.

Other examples of grafted silicone polymers corresponding to formula (IV) are, in particular, polydimethylsiloxanes (PDMS) on which are grafted, via a thiopropylene-type connecting chain, polymer units of the polyisobutyl (meth) acrylate type.

Preferably, the number-average molecular mass of the silicone polymers containing a polysiloxane skeleton grafted with non-silicone organic monomers, of the invention, ranges from 10,000 to 1,000,000 approximately and even more preferably from 10,000 to 100,000 approximately.

The grafted silicone polymers of the invention are preferably used in an amount ranging from 0.01 to 20% by weight relative to the total weight of the composition. More preferably, this amount ranges from 0.1 to 15% by weight and even more preferably from 0.5 to 10% by weight.

(2)—Aminosilicone(s)

According to the invention, the term aminosilicone is understood to denote any silicone containing at least one primary, secondary or tertiary amine or a quaternary ammonium group. Mention may thus be made of:

(a) the polysiloxanes referred to in the CTFA dictionary as "amodimethicone" and corresponding to the formula:

$$HO-\left[\begin{array}{c}CH_3\\|\\Si-O\\|\\CH_3\end{array}\right]_{x'}-\left[\begin{array}{c}OH\\|\\Si-O\\|\\(CH_2)_3\\|\\NH\\|\\(CH_2)_3\\|\\NH_2\end{array}\right]_{y'}-H \quad (II)$$

in which x' and y' are integers dependent on the molecular weight, generally such that the said number-average molecular weight is between 5000 and 500,000 approximately;

(b) cationic silicone polymers corresponding to the formula:

$$R'_aG_{3-a}-Si\,(OSiG_2)_n-(OSiG_bR'_2b)_m-O-SiG_{3-a}-R'_a \quad (III)$$

in which:

G is a hydrogen atom or a phenyl, OH or $C_1$–$C_6$ alkyl, for example methyl, group, a denotes the number 0 or an integer from 1 to 3, in particular 0, b denotes 0 or 1, and in particular 1, m and n are numbers such that the sum (n+m) can range especially from 1 to 2000 and in particular from 50 to 150, it being possible for n to denote a number from 0 to 1999 and in particular from 49 to 149 and it being possible for m to denote a number from 1 to 2000, and in particular from 1 to 10;

R' is a monovalent radical of formula —$C_qH_{2q}L$ in which q is a number from 2 to 8 and L is an optionally quaternized amine group chosen from the groups:

—NR"—CH$_2$—CH$_2$—N'(R")$_2$

—N(R")$_2$

—N$^⊕$(R")$_3$A$^-$

—N$^⊕$(R")$_3$A$^-$

—N$^⊕$(R")$_3$A$^-$

—N(R")—CH$_2$—CH$_2$—N$^⊕$R"H$_2$A$^-$, in which R" can denote hydrogen, phenyl, benzyl or a saturated monovalent hydrocarbon-based radical, for example an alkyl radical containing from 1 to 20 carbon atoms, and A$^-$ represents a halide ion such as, for example, fluoride, chloride, bromide or iodide.

A product corresponding to this definition is the polymer referred to as "trimethylsilylamodimethicone", corresponding to the formula:

$$(CH_2)_3Si-\left[\begin{array}{c}CH_3\\|\\O-Si\\|\\CH_3\end{array}\right]_n-\left[\begin{array}{c}OH\\|\\O-Si\\|\\(CH_2)_3\\|\\NH\\|\\(CH_2)_3\\|\\NH_2\end{array}\right]_m-OSi(CH_2)_3 \quad (IV)$$

in which n and m have the meanings given above (cf. formula III).

Such polymers are described, for example, in patent application EP-A-95238.

(c) Cationic silicone polymers corresponding to the formula:

$$(R_7)_3-Si-O-\left[\begin{array}{c}R_7\\|\\Si-O\\|\\R_7\end{array}\right]_r-\left[\begin{array}{c}R_8-CH_2-CHOH-CH_2-\overset{⊕}{N}(R_7)_3Q^⊖\\|\\Si-O\\|\\R_7\end{array}\right]_s-Si-(R_7)_3 \quad (V)$$

in which:

$R^7$ represents a monovalent hydrocarbon-based radical having from 1 to 18 carbon atoms, and in particular a $C_1$–$C_{18}$ alkyl or $C_2$–$C_{18}$ alkenyl radical, for example methyl;

$R_8$ represents a divalent hydrocarbon-based radical, in particular a $C_1$–$C_{18}$ alkylene radical or a divalent $C_1$–$C_{18}$ for example $C_1$–$C_8$, alkylenoxy radical;

$Q^-$ is a halide ion, in particular chloride;

r represents an average statistical value from 2 to 20 and in particular from 2 to 8;

s represents an average statistical value from 20 to 200 and in particular from 20 to 50.

Such polymers are described more particularly in U.S. Pat. No. 4,185,087.

A polymer falling within this category is the polymer sold by the company Union Carbide under the name "Ucar Silicone ALE 563.

When these silicone polymers are used, a particularly advantageous embodiment is their joint use with cationic and/or nonionic surfactants. It is possible to use, for example, the product sold under the name "Emulsion Cationic DC 929" by the company Dow Corning, which comprises, besides amodimethicone, a cationic surfactant comprising a mixture of products corresponding to the formula:

$$R_9-\overset{\overset{CH_3}{|}}{\underset{\underset{CH_3}{|}}{N^⊕}}-CH_3 \quad Cl^⊖$$

in which $R_9$ denotes alkenyl and/or alkyl radicals having from 14 to 22 carbon atoms, fatty acid derivatives of tallow, in combination with a nonionic surfactant of formula:

$$C_9H_{19}-C_6H_4-(OC_2H_4)_{10}-OH$$

known under the name "Nonoxynol 10".

It is also possible to use, for example, the product sold under the name "Cationic Emulsion DC 939" by the company Dow Corning, which comprises, besides amodimethicone, a cationic surfactant, trimethylcetylammonium chloride, in combination with a nonionic surfactant, trideceth-12.

Another commercial product which can be used according to the invention is the product sold under the name "Dow Corning Q2 7224" by the company Dow Corning, containing, in combination with the trimethylsilylamodimethicone of formula (IV), a nonionic surfactant of formula: $C_8H_{17}$—$C_6H_4$—$(OCH_2CH_2)_n$—OH where n=40, also known as octoxynol-40, another nonionic surfactant of formula: $C_{12}H_{25}$—$(OCH_2$—$CH_2)_n$—OH where n=6, also known as isolaureth-6, and glycol.

The hair compositions in accordance with the invention contain the aminosilicones defined above in weight contents which can be between 0.05% and 10%, preferably between 0.1% and 5% and even more preferably between 0.2% and 3%, relative to the total weight of the composition.

The vehicle, or support, for the detergent compositions according to the invention is preferably water or an aqueous-alcoholic solution of a lower alcohol such as ethanol, isopropanol or butanol.

The detergent compositions according to the invention have a final pH generally of between 3 and 10. Preferably, this pH is between 5.5 and 8. The pH can be adjusted to the desired value conventionally by adding a base (organic or inorganic) to the composition, for example aqueous ammonia or a primary, secondary or tertiary (poly)amine such as monoethanolamine, diethanolamine, triethanolamine, isopropanolamine or 1,3-propanediamine, or alternatively by adding an acid, preferably a carboxylic acid such as, for example, citric acid.

Needless to say, the detergent compositions according to the invention can also contain any common adjuvant encountered in the field of shampoos, such as, for example, fragrances, preserving agents, sequestering agents, thickeners, softeners, foam modifiers, dyes, pearlescent agents, moisturizers, antidandruff agents, antiseborrhoeic agents, vitamins or sunscreens, and the like.

Needless to say, a person skilled in the art will take care to select this or these optional complementary compounds and/or the amounts thereof such that the advantageous properties intrinsically associated with the ternary combination (washing base+cationic polymer+two specific silicones) in accordance with the invention are not, or are not substantially, adversely affected by the addition or additions envisaged.

These compositions can be in the form of more or less thickened liquids, creams or gels and are mainly suitable for washing, caring for and/or styling the hair. They can also be in the form of rinse-out lotions.

When the compositions in accordance with the invention are used as standard shampoos, they are simply applied to wet hair and the lather generated by massaging or friction with the hands is then removed, after optionally leaving it to stand on the hair for a period of time, by rinsing with water, it being possible for the operation to be repeated one or more times.

A subject of the invention is also a process for washing and conditioning keratin fibres such as the hair, which consists in applying an effective amount of a composition as defined above to the said wet fibres, and then in rinsing them with water after optionally leaving the composition to stand on the fibres for a period of time.

As indicated above, the compositions in accordance with the invention give the hair, after rinsing, a noteworthy styling effect which is shown in particular by an ease of styling and of hold, as well as giving markedly improved volume and lightness.

Concrete, but in no way limiting, examples illustrating the invention will now be given.

EXAMPLE 1

Two shampoo compositions, one in accordance with the invention (composition A) and the other a comparative composition (composition B), were prepared;

|  | A Invention | B Comparative |
|---|---|---|
| Sodium lauryl ether sulphate (70/30 $C_{12}/C_{14}$) containing 2.2 mol of ethylene oxide, as an aqueous solution containing 28% AM (AM = active material) | 14 gAM | 14 gAM |
| Cocoylbetaine containing 32% AM (*) | 3.2 gAM | 3.2 gAM |
| Cationic polymer (**) | 0.1 g | 0.1 g |
| Aminosilicone (***) | 1.05 gAM | — |
| Grafted silicone polymer (****) | 2 gAM | 2 gAM |
| Mixture of 1-hexadecyloxyoctadodecanol and cetyl alcohol | 2.5 g | 2.5 g |
| Coconut acid monoisopropanolamide | 0.6 g | 0.6 g |
| Citric acid, qs pH | 5.2 | 5.2 |
| Demineralized water qs | 100 g | 100 g |

(*) Dehyton AB 30 from Henkel
(**): Guar gum modified with 2,3-epoxypropyltrimethyl-ammonium chloride, sold under the name Jaguar C13 S by the company Rhône-Poulenc
(***): Amodimethicone sold as a cationic emulsion containing 35% active material, under the name Fluid DC 939 by the company Dow Corning
(****): Polydimethyl/methylsiloxane containing 3-propylthio polymethacrylic acid/polyisobutyl methacrylate/methacrylic acid groups, pre-neutralized with aqueous ammonia and sold as an aqueous solution containing 10% active material under the name VS 80 by the company 3M.

Shampooing is carried out by applying about 12 g of composition A to premoistioned hair. The shampoo is worked into a lather and is then rinsed out thoroughly with water.

The same procedure as above is carried out with the comparative composition B.

A panel of experts evaluates the disentangling of the wet hair, the disentangling of the dried hair, the ease of styling, the softness, the volume, the liveliness and the smoothness of the dried hair.

All the experts indicate a marked improvement in these properties for the hair treated with composition A according to the invention.

Furthermore, the hair treated with composition A dries faster.

EXAMPLE 2

| A shampoo of the following composition was prepared: | |
|---|---|
| Sodium lauryl ether sulphate (70/30 $C_{12}/C_{14}$) containing 2.2 mol of ethylene oxide, as an aqueous solution containing 28% AM | 14 gAM |
| Cocoylbetaine containing 32% AM (*) | 3.2 gAM |

-continued

A shampoo of the following composition was prepared:

| | |
|---|---|
| Sodium lauryl ether sulphate (70/30 $C_{12}/C_{14}$) containing 2.2 mol of ethylene oxide, as an aqueous solution containing 28% AM | 14 gAM |
| Cationic polymer (**) | 0.1 g |
| Aminosilicone (***) | 1.05 gAM |
| Grafted silicone polymer (*****) | 0.5 gAM |
| Mixture of 1-hexadecyloxyoctadodecanol and cetyl alcohol | 2.5 g |
| Coconut acid monoisopropanolamide | 0.6 g |
| 2-Amino-2-methyl-1-propanol | 0.125 g |
| Citric acid, qs pH | 5.2 |
| Demineralized water qs | 100 g |

(*) Dehyton AB 30 from Henkel
(**): Guar gum modified with 2,3-epoxypropyltrimethyl-ammonium chloride, sold under the name Jaguar C13 S by the company Rhône-Poulenc
(***): Amodimethicone sold as a cationic emulsion containing 35% active material, under the name Fluid DC 939 by the company Dow Corning
(*****): Copolymer of acrylic acid (20% by weight), tert-butyl acrylate (60% by weight) and polydimethyl-siloxane methacrylate (20% by weight)

What is claimed is:

1. A detergent and conditioning hair composition comprising a washing base and a conditioning system, said conditioning system comprising at least one cationic polymer and a mixture of at least one aminosilicone and of at least one grafted silicone polymer, said grafted silicone polymer comprising a polysiloxane portion and a portion containing a non-silicone organic chain, wherein one of said two portions constitutes the skeleton of the silicone polymer, and the other portion is grafted onto said skeleton, and further wherein said washing base is present at a weight content ranging from 4% to 50% relative to the total weight of the composition.

2. A composition according to claim 1, wherein said composition further comprises a cosmetically acceptable medium and wherein said at least one grafted silicone polymer is a polymer having a non-silicone organic skeleton grafted with at least one monomer containing a polysiloxane, a polymer having a polysiloxane skeleton grafted with at least one non-silicone organic monomer, or a mixture thereof.

3. A composition according to claim 2, wherein said at least one grafted silicone polymer comprises an organic skeleton formed from units of at least one non-silicone organic monomer, on which is grafted, inside said skeleton, at least one polysiloxane macromer.

4. A composition according to claim 3, wherein said non-silicone organic monomers constituting the skeleton of the at least one grafted silicone polymer are monomers containing ethylenic unsaturation which are polymerizable via a radical route, monomers which are polymerizable by polycondensation, or monomers which are polymerizable by a mechanism involving ring opening.

5. A composition according to claim 1, said composition comprising a mixture of at least one aminosilicone and at least one grafted silicone polymer, said silicone polymer comprising:
up to 98% by weight of at least one lipophilic monomer, A, relative to the total weight of the monomers A, B, and C, of low polarity containing ethylenic unsaturation, which is polymerizable via a radical route;
up to 98% by weight of at least one polar hydrophilic monomer, B, relative to the total weight of the monomers A, B, and C, containing ethylenic unsaturation, which is copolymerizable with the A-type monomer(s);
from 0.01% to 50% by weight of at least one polysiloxane macromer, C, relative to the total weight of the monomers A, B, and C, said macromer C having the formula (I)

$$X(Y)_n Si(R)_{3-m} Z_m \qquad (I)$$

wherein:
X represents a vinyl group that is copolymerizable with the monomers A and B;
Y represents a divalent bonding group;
R represents a hydrogen, a $C_1$–$_6$ alkyl or alkoxy or a $C_6$–$C_{12}$ aryl;
Z represents a monovalent polysiloxane unit having a number-average molecular weight of at least 500;
n is 0 or 1;
and m is an integer ranging from 1 to 3.

6. A composition according to claim 5, wherein said at least one lipophilic monomer A is an acrylic or methacrylic acid ester of a $C_1$–$C_{18}$ alcohol, styrene, a polystyrene macromer, vinyl acetate, vinyl propionate, α-methylstyrene, tert-butylstyrene, butadiene, cyclohexadiene, ethylene, propylene, vinyltoluene, an acrylic or methacrylic acid ester of 1,1-dihydroperfluoroalkanol, an acrylic or methacrylic acid ester of an ω-hydridofluoroalkanol, an acrylic or methacrylic acid ester of a fluoroalkylsulphoamido alcohol, an acrylic or methacrylic acid ester of a fluoroalkyl alcohol, or an acrylic or methacrylic acid ester of a fluoroether alcohol.

7. A composition according to claim 6, wherein said at least one lipophilic monomer A is n-butyl methacrylate, isobutyl methacrylate, tert-butyl acrylate, tert-butyl methacrylate, 2-ethylhexyl methacrylate, methyl methacrylate, 2-(N-methylperfluorooctanesulphonamido) ethyl acrylate, or 2 (butylperfluorooctanesulphonamido) ethyl acrylate.

8. A composition according to claim 5, wherein said at least one polar monomer B is acrylic acid, methacrylic acid, N,N-dimethylacrylamide, dimethylaminoethyl methacrylate, quaternized dimethylaminoethyl methacrylate, (meth)acrylamide, N-t-butylacrylamide, maleic acid, maleic anhydride or a semiester thereof, a hydroxyalkyl (meth)acrylate, diallyldimethylammonium chloride, vinylpyrrolidone, a vinyl ether, maleimide, vinylpyridine, vinylimidazole, a heterocyclic vinyl polar compound, styrene sulphonate, allyl alcohol, vinyl alcohol, or vinyl caprolactam.

9. A composition according to claim 8, wherein said at least one polar monomer B is an acrylic acid, N,N-dimethylacrylamide, dimethylaminoethyl methacrylate, quaternized dimethylaminoethyl methacrylate, or vinylpyrrolidone.

10. A composition according to claim 5, wherein said at least one polysiloxane macromer C has the formula (II):

$$CHR^1 = CR^2 - \overset{O}{\underset{\|}{C}} - O - (CH_2)_{\overline{q}} - (O)_{\overline{p}} - Si(R^3)_{3-m} - (O - \underset{CH_3}{\overset{CH_3}{\underset{|}{Si}}})_{\overline{r}} - R^4 \qquad (II)$$

in which:
$R^1$ is hydrogen or —COOH;
$R^2$ is hydrogen, methyl or —$CH_2COOH$;

R³ is $C_1$–$C_6$ alkyl, alkoxy, or alkylamino, $C_6$–$C_{12}$ aryl or hydroxyl;

R⁴ is $C_1$–$C_6$ alkyl, alkoxy or alkylamino, $C_6$–$C_{12}$ aryl or hydroxyl;

q is an integer ranging from 2 to 6;

p is 0 or 1;

r is an integer ranging from 5 to 700; and m is an integer ranging from 1 to 3.

11. A composition according to claim 10, wherein said at least one polysiloxane macromer C has the formula:

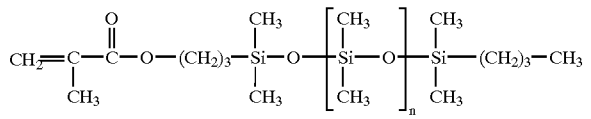

wherein n is an integer ranging from 5 to 700.

12. A composition according to claim 1, wherein said mixture of at least one aminosilicone and at least one grafted silicone polymer is obtained by radical polymerization starting with a monomer mixture comprising:

a) 60% by weight of tert-butyl acrylate relative to the total weight of the monomers present;

b) 20% by weight of acrylic acid relative to the total weight of the monomers present; and c) 20% by weight of a silicone macromer of formula:

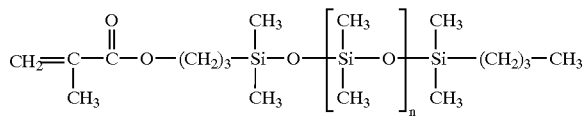

relative to the total weight of the monomers present, and wherein n is an integer ranging from 5 to 700.

13. A composition according to claim 1, wherein said mixture of at least one aminosilicone and at least one grafted silicone polymer is obtained by radical polymerization starting with the monomer mixture comprising:

a) 80% by weight of tert-butyl acrylate relative to the total weight of the monomers present; and b) 20% by weight of a silicone macromer having the formula:

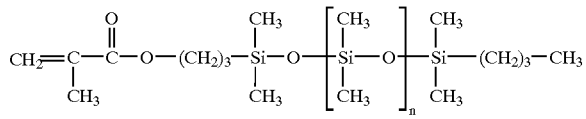

relative to the total weight of the monomers present, and wherein n is an integer ranging from 5 to 700.

14. A composition according to claim 2, wherein said at least one grafted silicone polymer comprising a non-silicone organic skeleton grafted with at least one monomer containing a polysiloxane has a number-average molecular weight ranging from 10,000 to 2,000,000 and a glass transition temperature Tg or a crystalline melting point Tm of at least −20° C.

15. A composition according to claim 2, said composition comprising at least one grafted silicone polymer comprising a non-silicone organic skeleton grafted with at least one monomer containing a polysiloxane, said composition being obtained by reactive extrusion of a polysiloxane macromer having a terminal reactive function with a polyolefin-type polymer containing reactive groups which react with said reactive terminal function of the polysiloxane macromer to form a covalent bond, thereby allowing grafting of the silicone to the skeleton of the polyolefin-type polymer.

16. A composition according to claim 15, wherein said reactive polyolefin-type polymer is a polyethylene or a polymer of an ethylene-derived monomer containing reactive functions, which reactive functions react with said terminal function of the polysiloxane macromer.

17. A composition according to claim 15, wherein said reactive polyolefin-type polymer is a copolymer of ethylene or of an ethylene derivative and of a monomer containing a carboxylic function, an acid anhydride function, an acid chloride function, an ester function, or an isocyanate function.

18. A composition according to claim 15, wherein said polysiloxane macromer comprises a terminal functional group, wherein said terminal functional group is an alcohol, a thiol, an epoxy group or a primary or secondary amine, and further wherein said terminal functional group is not sterically hindered from reacting to form a stable compound.

19. A composition according to claim 15, wherein said polysiloxane macromer is a polysiloxane having the formula (III):

in which T is $NH_2$, NHR', an epoxy, an OH, or an SH function; $R^5$, $R^6$, $R^7$ and R', independently represent a $C_{1-6}$ alkyl, phenyl, benzyl, $C_6$–$C_{12}$ alkylphenyl or hydrogen; s is a number ranging from 2 to 100; t is a number from 0 to 1000; and y is a number ranging from 1 to 3.

20. A composition according to claim 2, said composition comprising at least one grafted silicone polymer having a polysiloxane skeleton grafted with at least one non-silicone organic monomer, wherein said at least one non-silicone organic monomer is grafted inside said skeleton.

21. A composition according to claim 20, wherein said at least one grafted silicone polymer having a polysiloxane skeleton grafted with at least one non-silicone organic monomer is obtained by radical copolymerization between at least one non-silicone anionic organic monomer containing ethylenic unsaturation and/or a non-silicone hydrophobic organic monomer containing ethylenic unsaturation, and a polysiloxane containing in its chain at least one functional group reacting with said ethylenic unsaturations of said at least one non-silicone monomer.

22. A composition according to claim 21, wherein said at least one anionic organic monomer containing ethylenic unsaturation is a linear or branched, unsaturated carboxylic acid.

23. A composition according to claim 22, wherein said at least one anionic organic monomer containing ethylenic unsaturation is acrylic acid, methacrylic acid, maleic acid, maleic anhydride, itaconic acid, fumaric acid or crotonic acid, or the alkali metal, alkaline-earth metal or ammonium salt of any of said monomers.

24. A composition according to claim 21, wherein said hydrophobic organic monomer containing ethylenic unsaturation is an acrylic acid ester of an alkanol or a methacrylic acid ester of an alkanol, or a mixture thereof.

25. A composition according to claim 24, wherein said alkanol is a $C_1$–$C_{18}$ alkanol.

26. A composition according to claim 24, wherein said hydrophobic organic monomer containing ethylenic unsaturation is isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)

acrylate, methyl (meth)acrylate, tert-butyl (meth)acrylate, tridecyl (meth)acrylate or stearyl (meth)acrylate, or a mixture thereof.

27. A composition according to claim 20, wherein said at least one grafted silicone polymer comprises, on said polysiloxane skeleton, at least one organic group of anionic nature obtained by radical homopolymerization of at least one anionic monomer of unsaturated carboxylic acid type, partially or totally neutralized in the form of a salt.

28. A composition according to claim 20, wherein said at least one grafted silicone polymer is a silicone polymer containing in its structure the group of formula (IV):

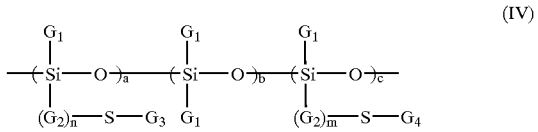

(IV)

in which the radicals $G_1$ are identical or different and represent hydrogen or a $C_1$–$C_{10}$ alkyl radical or a phenyl radical; the radicals $G_2$ are identical or different and represent a $C_1$–$_{10}$ alkylene group; $G_3$ represents a polymer residue resulting from the homopolymerization of at least one anionic monomer containing ethylenic unsaturation; $G_4$ represents a polymer residue resulting from the homopolymerization of at least one hydrophobic monomer containing ethylenic unsaturation; m and n are equal to 0 or 1; a is an integer ranging from 0 to 50; b is an integer which ranges from 10 to 350, and c is an integer ranging from 0 to 50; with the proviso that one of the integers a and c is not 0.

29. A composition according to claim 28, wherein said at least one grafted silicone polymer is a silicone polymer containing in its structure the group of formula (IV) wherein:

the radicals $G_1$ represent a $C_1$–$C_{10}$ alkyl radical;
n is 1; the radicals $G_2$ represent a divalent $C_1$–$C_3$ radical;
$G_3$ represents a polymer residue resulting from the homopolymerization of at least one monomer of the carboxylic acid type containing ethylenic unsaturation; or
$G_4$ represents a polymer residue resulting from the homopolymerization of at least one monomer of the ($C_1$–$C_{10}$)alkyl (meth)acrylate type.

30. A composition according to claim 28, wherein said at least one grafted silicone polymer is a silicone polymer containing in its structure the group of formula (IV) wherein:

the radicals $G_1$ denote a methyl radical;
n is 1; the radicals $G_2$ represent a propylene radical;
$G_3$ represents a polymer residue resulting from the homopolymerization of at least acrylic acid and/or methacrylic acid; and
$G_4$ represents a polymer residue resulting from the homopolymerization of at least one monomer of the isobutyl or methyl (meth)acrylate type.

31. A composition according to claim 20, wherein the number-average molecular mass of the silicone polymer containing a polysiloxane skeleton grafted with at least one non-silicone organic monomer ranges from 10,000 to 1,000,000.

32. A composition according to claim 31, wherein the number-average molecular mass of the silicone polymer containing a polysiloxane skeleton grafted with at least one non-silicone organic monomer ranges from 10,000 to 100,000.

33. A composition according to claim 1, wherein said washing base comprises at least one surfactant selected from anionic, amphoteric, nonionic, zwitterionic and cationic surfactants.

34. A composition according to claim 1, wherein said at least one cationic polymer is a quaternary cellulose ether derivative, a cyclopolymer or a cationic polysaccharide.

35. A composition according to claim 34, wherein said cyclopolymer is a copolymer of dimethyldiallylammonium chloride and of acrylamide.

36. A composition according to claim 34, wherein said quaternary cellulose ether derivative is formed by the reaction of hydroxyethylcellulose with an epoxide and is substituted with a trimethylammonium group.

37. A composition according to claim 34, wherein said cationic polysaccharide is a guar gum modified with a 2,3-epoxypropyltrimethylammonium salt.

38. A composition according to claim 1, wherein said at least one amino-silicone is:

(a) amodimethicone of the formula (II):

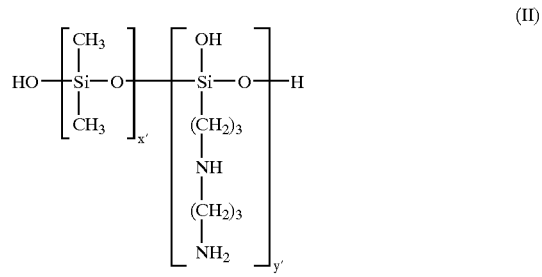

(II)

in which x' and y' are integers dependent on the molecular weight;

(b) a cationic silicone polymer having the formula:

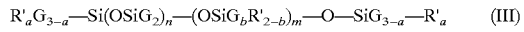

(III)

in which:
G is a hydrogen atom or a phenyl, OH or $C_1$–$C_8$ alkyl group,
a represents the number 0 or an integer from 1 to 3,
b represents 0 or 1,
m and n are numbers such that the sum (n+m) ranges from 1 to 2000, n represents a number from 0 to 1999, and m represents a number from 1 to 2000;
R' is a monovalent radical of formula —$C_qH_{2q}$L in which q is a number from 2 to 8 and L is an optionally quaternized amine group selected from:

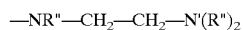

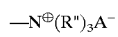

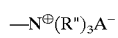

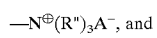, and

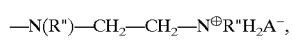

in which R" represents hydrogen, phenyl, benzyl or a saturated monovalent hydrocarbon-based radical, and A⁻ represents a halide ion; or (c) a cationic silicone polymer having the formula (V):

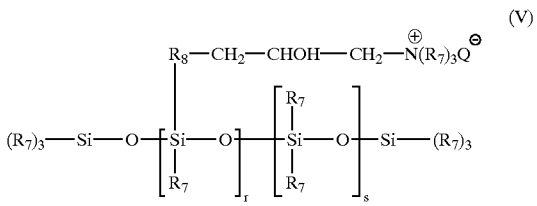

in which:
R$^7$ represents a monovalent hydrocarbon-based radical having from 1 to 18 carbon atoms;
R$_8$ represents a divalent hydrocarbon-based radical or a divalent C$_1$–C$_{18}$ alkylenoxy radical;
Q$^-$ is a halide ion;
r represents an average statistical value ranging from 2 to 20; and
s represents an average statistical value ranging from 20 to 200.

39. A composition according to claim 38, wherein said polysiloxane having the formula (II) has a number average molecular weight ranging from 5000 to 500,000.

40. A composition according to claim 38, wherein in said formula (III), G is a methyl group.

41. A composition according to claim 38, wherein in said formula (III), a is 0.

42. A composition according to claim 38, wherein in said formula (III), b is 1.

43. A composition according to claim 38, wherein in said formula (III), said sum (n+m) ranges from 50 to 150.

44. A composition according to claim 38, wherein in said formula (III), n ranges from 49 to 149.

45. A composition according to claim 38, wherein in said formula (III), m ranges from 1 to 10.

46. A composition according to claim 38, wherein R" in (b) represents a saturated monovalent hydrocarbon-based radical, which radical is an alkyl radical containing from 1 to 20 atoms.

47. A composition according to claim 38, wherein in said formula (III), A$^-$ represents fluoride, chloride, bromide, or iodide.

48. A composition according to claim 38, wherein in said formula (V), R$^7$ is a C$_1$–C$_{18}$ alkyl or a C$_2$–C$_{18}$ alkenyl radical.

49. A composition according to claim 48, wherein R$^7$ is methyl.

50. A composition according to claim 38, wherein in said formula (V), R$_8$ is a C$_1$–C$_{18}$ alkylene radical.

51. A composition according to claim 38, wherein in said formula (V), R$_8$ is a C$_1$–C$_8$ alkylenoxy radical.

52. A composition according to claim 38, wherein in said formula (V), Q$^-$ is chloride.

53. A composition according to claim 38, wherein in said formula (V), r represents an average statistical value ranging from 2 to 8.

54. A composition according to claim 38, wherein in said formula (V), s represents an average statistical value ranging from 20 to 50.

55. A composition according to claim 1, wherein said washing base is present at a weight content ranging from 10% to 35% relative to the total weight of the composition.

56. A composition according to claim 55, wherein said washing base is present at a weight content ranging from 12% to 25% relative to the total weight of the composition.

57. A composition according to claim 1, wherein said at least one cationic polymer is present at a weight content ranging from 0.001% to 10% relative to the total weight of the composition.

58. A composition according to claim 57, wherein said at least one cationic polymer is present at a weight content ranging from 0.005% to 5% relative to the total weight of the composition.

59. A composition according to claim 58, wherein said at least one cationic polymer is present at a weight content ranges from 0.01% to 3% relative to the total weight of the composition.

60. A composition according to claim 1, wherein said at least one grafted silicone polymer is present at a weight content ranging from 0.01% to 20% relative to the total weight of the composition.

61. A composition according to claim 60, wherein said at least one grafted silicone polymer is present at a weight content ranging from 0.1% to 15% relative to the total weight of the composition.

62. A composition according to claim 61, wherein said at least one grafted silicone polymer is present at a weight content ranging from 0.5% to 10% relative to the total weight of the composition.

63. A composition according to claim 1, wherein said at least one aminosilicone is present at a weight content ranging from 0.05 to 10% relative to the total weight of the composition.

64. A composition according to claim 63, wherein said at least one aminosilicone is present at a weight content ranging from 0.1 to 5% relative to the total weight of the composition.

65. A composition according to claim 1, said composition having a pH ranging from 3 to 10.

66. A method for cleaning and/or styling and/or conditioning hair, said method comprising applying an effective amount of the detergent and conditioning composition according to claim 1 to said hair.

67. The method according to claim 66, wherein said method further comprises wetting said hair before the application of said detergent and conditioning composition.

68. The method according to claim 67, wherein said method further comprises rinsing said hair following the application of said detergent and conditioning composition.

69. The method according to claim 68, wherein said method further comprises allowing said composition to remain on said wetted hair after said application and before said rinsing.

70. The composition according to claim 1, wherein said composition is in the form of a thickened liquid, a cream, a gel, or a rinse-out lotion.

71. A method for improving the styling effect of a detergent hair composition comprising at least one cationic polymer and at least one grafted silicone polymer, said method comprising incorporating into said detergent composition an effective amount of an aminosilicone for improving the styling effect of a detergent hair composition wherein said detergent hair composition further contains a washing base present at a weight content ranging from 4% to 50% relative to the total weight of the composition.

72. A composition according to claim 20, wherein, additionally, said at least one organic monomer containing no silicone is grafted on at least one end of said polysiloxane skeleton.

73. A composition according to claim 3, wherein, additionally, at least one polysiloxane macromer is grafted on at least one end of said organic skeleton.

74. A composition according to claim 65, said composition having a pH ranging from 5.5 to 8.

75. A composition according to claim 64, wherein said at least one aminosilicone is present at a weight content ranging from 0.2% to 3% relative to the total weight of the composition.

76. A composition according to claim 25, wherein said alkanol is a $C_1$–$C_{12}$ alkanol.

77. A method for making the composition according to claim 1, said method comprising reacting a polysiloxane with at least one non-silicone organic compound, said compound having a functional group capable of reacting with a functional group or groups on said polysiloxane, whereby said reaction forms a covalent bond, wherein said composition further comprises 4%–50% by weight of a washing base, at least one aminosilicone, and at least one cationic polymer.

* * * * *

UNITED STATES PATENT AND TRADEMARK OFFICE
CERTIFICATE OF CORRECTION

PATENT NO.    : 6,451,747 B1
DATED         : September 17, 2002
INVENTOR(S)   : Decoster It is certified that error appears in the above-identified patent and that said Letters Patent is hereby corrected as shown below:

Title Page,
Item (57), delete the ABSTRACT in its entirety and substitute therefore:
-- A detergent and hair conditioning composition having a washing base and a conditioning system, which has at least one cationic polymer and a mixture of at least one aminosilicone and of at least one grafted silicone polymer. --

Column 22,
Line 6, "(I)" should read -- (I): --.
Line 14, "$C_{1-6}$ alkyl" should -- $C_1$-$C_6$ alkyl --.
Line 36, "2 (butylperfluorooctanesulphonamido)" should read
-- 2-(butylperfluorooctanesulphonamido) --.

Column 24,
Lines 28-29, "$C_{1-6}$ alkyl," should read -- $C_1$-$C_6$ alkyl, --.

Column 25,
Line 23, "$C_{1-10}$ alkylene" should read -- $C_1$-$C_{10}$ alkylene --.

Column 26,
Lines 23-32, in the structure for formula (II):

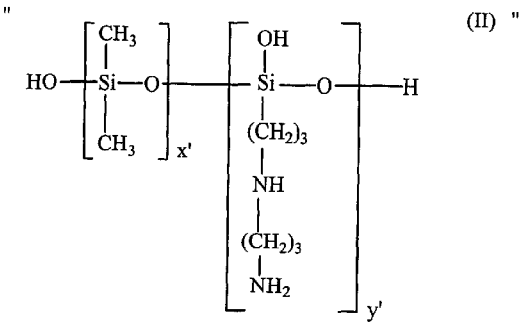

should read

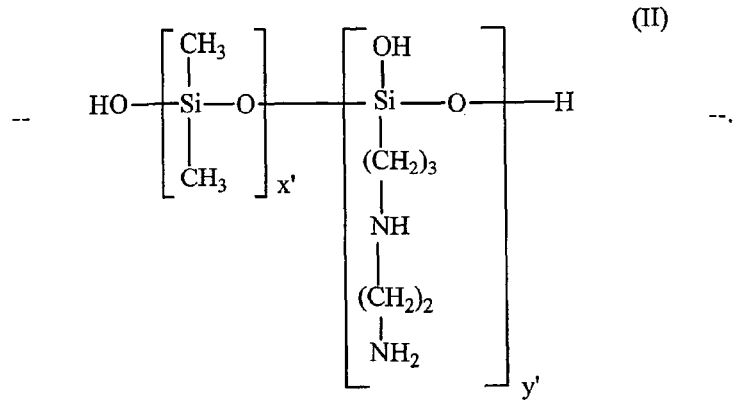

UNITED STATES PATENT AND TRADEMARK OFFICE
CERTIFICATE OF CORRECTION

PATENT NO.    : 6,451,747 B1
DATED         : September 17, 2002
INVENTOR(S)   : Decoster It is certified that error appears in the above-identified patent and that said Letters Patent is hereby corrected as shown below:

<u>Column 28,</u>
Line 9, "ranges" should read -- ranging --.
Line 17, "0. 1 %" should read -- 0.1% --.
Line 55, after "composition", insert a comma.

Signed and Sealed this

Twenty-eighth Day of January, 2003

JAMES E. ROGAN
*Director of the United States Patent and Trademark Office*